United States Patent [19]

Skotnicki et al.

[11] Patent Number: 4,808,612
[45] Date of Patent: Feb. 28, 1989

[54] 2-ARYLBENZO(B)(1,6)NAPHTHYRIDINES AS INHIBITORS OF INTERLEUKIN 1

[75] Inventors: Jerauld S. Skotnicki, Chadds Ford; Steven C. Gilman, Newtown Square, both of Pa.

[73] Assignee: American Home Products Corporation, New York, N.Y.

[21] Appl. No.: 47,970

[22] Filed: May 7, 1987

[51] Int. Cl.$^4$ .............................................. A61K 31/44
[52] U.S. Cl. ..................................................... 514/290
[58] Field of Search ................................. 514/299, 290

Primary Examiner—Stanley J. Friedman
Attorney, Agent, or Firm—George Tarnowski

[57] ABSTRACT

There is disclosed a method for the treatment of inflammatory conditions and of collegenase-induced tissue destruction which comprises the administration of a therapeutically effective amount of a compound of the formula

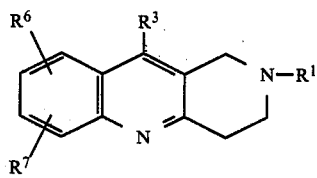

wherein $R^1$ is phenyl or naphthyl, or phenyl or naphthyl substituted with halo, lower alkyl, lower alkyl carbonyl, benzoyl, carboxy, lower alkoxycarbonyl, $OR^2$, $N(R^2)_2$, $CON(R^2)_2$, $SO_3R^2$, $SO_2N(R^2)_2$, phenylsulfonyl, lower alkylsulfonyl, cyano nitro or trifluoromethyl;

$R^2$ is hydrogen, lower alkyl or phenyl;

$R^3$ is halo, morpholino, 4-methylpiperazino $R^4NNHR^5$, $NR^4R^5$, $OR^5$, $SR^5$, $R^4NCH_2CH_2OCH_3$, $SCH_2CH_2CH_2NH_2$ or

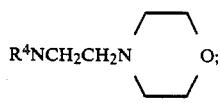

$R^4$ is hydrogen or lower alkyl;

$R^5$ is hydrogen, lower alkyl, lower alkanoyl, lower cycloalkyl or phenyl; and $R^6$ and $R^7$ are each independently, hydrogen, halo, nitro, lower alkoxy, lower alkyl, cyano, trifluoromethyl, phenyl, carboxy or lower alkoxycarbonyl;

which compounds, by virtue of their ability to inhibit interleukin 1, are useful as antiinflammatory agents and in treatment of disease states involving enzymatic tissue destruction, and are also intermediates in the preparation of other compounds which possess identical activities.

12 Claims, No Drawings

2-ARYLBENZO(B)(1,6)NAPHTHYRIDINES AS INHIBITORS OF INTERLEUKIN 1

This invention relates to a method for treating inflammation by the use of compounds possessing interleukin 1 (IL 1) antagonist activity and having antiinflammatory activity.

Interleukin 1 (IL 1) is a peptide hormone exhibiting a number of immune and inflammatory actions [Dinarello, *Rev. Inf. Dis.* 6, 51 (1984)]. IL 1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL 1 was originally shown to augment the proliferation of T lymphocytes for which it was named lymphocyte activating factor (LAF), and is believed to be important for the generation of T cell-dependent immune responses.

There is evidence to suggest a relationship between IL 1 and pathology in various diseases, particularly immunoinflammatory disorders such as rheumatoid arthritis [Dinarello et al., *Ann. Rev. Med.* 37, 173 (1986)]. IL 1 induces acute inflammatory responses producing soft tissue swelling (edema and erythema) [Granstein et al., *J. Clin. Invest.*, 77, 1010 (1986)]. It is a chemoattractant for polymorphonuclear leukocytes (PMN) and induces the activation and migration of these cells into tissues. IL 1 also stimulates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1283 (1986)] and hypothalamic tissue. This effect on the hypothalamus is thought to be responsible for fever production. IL 1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chrondrocytes, and fibroblasts [Dayer et al., *Science*, 195, 181 (1977) and Postlethwaite et al., *J. Exp. Med.*, 157, 801 (1983)]. Furthermore, IL 1 induces hyperproliferation of dermal and synovial fibroblasts and is a potent inducer of bone resorption [Wood et al., *J. Immunol.*, 134, 895 (1985) and Gilman and Kimball, *Agents and Actions*, 16, 468 (1985)].

Finally, IL 1 mediates acute phase reactions including alterations in plasma divalent cations, increased synthesis by liver cells of acute phase proteins (C-reactive protein, serum amyloid A, etc.) and fever. Accordingly, compounds which have IL 1 antagonist activity and thereby inhibit the biological effects of IL 1 can be advantageously used to block pathologies in which one or more of these events occur such as rheumatoid arthritis, osteoarthritis and related disorders [Rodnan and Schumacher, eds, "Primer on the Arthritic Diseases" 8 ed. Altanta, 1983], psoriasis and other inflammatory/proliferative skin disorders as well as diseases in which the secretion of collagenase (and other tissue hydrolysing neutral proteinases) has been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

It has now been found that certain 2-arylbenzo[b][1,6-]naphthyridines antagonize the activity of IL 1, and so are useful as antiinflammatory agents and in the treatment of pathologies whose etiology is collagenase-based tissue destruction. Of the compounds used in the present invention, those in which $R^1$ is fluorophenyl are disclosed in U.S. Pat. Nos. 3,637,706 and 3,674,790 wherein these compounds are taught to be pharmacologically active as central nervous system depressants. The remaining compounds used in the present invention are novel 2-arylbenzo[b][1,6]naphthyridines.

The present invention is directed to a method for the treatment of inflammatory conditions and of collagenase-induced tissue destruction which comprises the administration of a therapeutically effective amount of a compound having the formula:

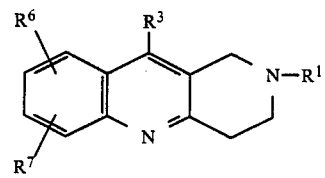

wherein $R^1$ is phenyl or naphthyl, or phenyl or naphthyl substituted with halo, lower alkyl, lower alkyl carbonyl, benzoyl, carboxy, lower alkoxycarbonyl, $OR^2$, $N(R^2)_2$, $CON(R^2)_2$, $SO_3R^2$, $SO_2N(R^2)_2$, phenylsulfonyl, lower alkylsulfonyl, cyano, nitro or trifluoromethyl;

$R^2$ is hydrogen, lower alkyl or phenyl;

$R^3$ is halo, morpholino, 4-methylpiperazino, $R^4NNHR^5$, $NR^4R^5$, $OR^5$, $SR^5$, $R^4NCH_2CH_2OCH_3$, $SCH_2CH_2CH_2NH_2$ or

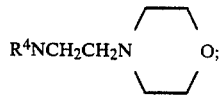

$R^4$ is hydrogen or lower akyl;

$R^5$ is hydrogen, lower alkyl, lower alkanoyl, lower cycloalkyl or phenyl; and $R^6$ and $R^7$ are each independently, hydrogen, halo, nitro, lower alkoxy, lower alkyl, cyano, trifluoromethyl, phenyl, carboxy or lower alkoxycarbonyl.

The terms "lower alkyl" and "lower alkoxy" refers to moieties having 1 to 6 carbon atoms in the carbon chain. The term "lower alkanoyl" refers to the moiety RCO— wherein R is an alkyl group having 1 to 6 carbon atoms. The term "lowercycloalkyl" refers to a saturated ring having 4 to 7 carbon atoms. The term "halo" refers to fluoro, chloro and bromo.

The compounds of the invention, in addition to processing IL 1 antagonist activity, are also intermediates for producing certain of the compounds among those embraced by the formula

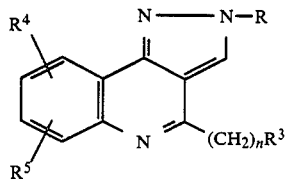

wherein

R is lower alkyl, carboxy lower alkyl, alkoxy carbonyl lower alkyl, cyano lower alkyl, nitro lower alkyl, hydroxy lower alkyl, lower alkoxy lower alkyl, $COR^1$, $CO_2R^2$, $CON(R^2)_2$, $SO_2R^1$, phenyl, naphthyl, pyridyl, quinolinyl or phenyl, naphthyl, pyridyl or quinolinyl substituted by halo, lower alkyl, lower alkoxy, nitro, cyano, amino, mono-lower alkyl amino, di-lower alkyl amino, carboxy, lower alkoxycarbonyl or hydroxy;

$R^1$ is phenyl, phenyl lower alkyl, naphthyl, pyridyl, quinolinyl, pyrazinyl, pyrimidinyl, pyridinyl, pyridazinyl, quinoxalinyl, quinazolinyl or any of the foregoing substituted with halo, lower alkyl, carboxy, cyano, nitro, lower alkylsulfonyl, lower alkoxy carbonyl or lower alkyl substituted by fluoro, carboxy, cyano, nitro or lower alkoxy carbonyl;

$R^2$ is hydrogen, lower alkyl, phenyl or benzyl;

$R^3$ is hydrogen, $R^1$, $OR^1$, $SR^1$ or $NR^2R^1$, $NH_2$, $NR^6R^1$ or $NR^6R^7$;

$R^4$ and $R^5$ are each independently, hydrogen, halo, lower alkoxy, lower alkyl, trifluoromethyl, cyano, nitro, carboxy or lower alkoxycarbonyl;

$R^6$ is carbamoyl, phenylcarbamoyl, or halophenylcarbamoyl;

$R^7$ is hydrogen or lower alkyl; and n is 1-5.

The compounds of the invention can be prepared by the reaction of 1,4-dioxa-8-azaspiro[4.5]decane with a suitable halo-$R^1$ reactant, and following ketal hydrolysis, the reaction of the resultant intermediate with a suitably substituted amino benzoic acid in the presence of a halogenating agent to yield an intermediate halogenated benzo[b][1,6]naphthyridine:

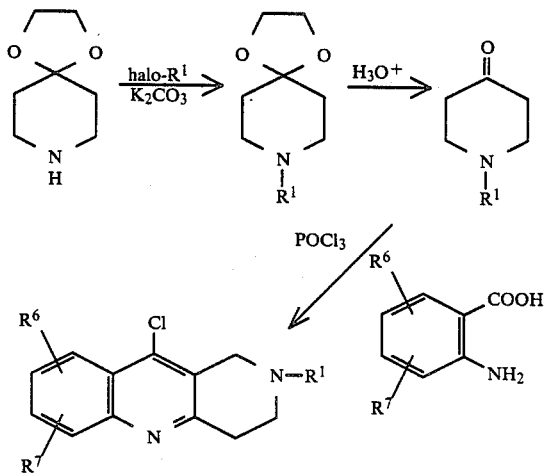

In the final step, the intermediate halogenated benzo[b][1,6]naphthyridine is reacted with a suitably substituted $R^3$-containing reactant to yield the desired final product:

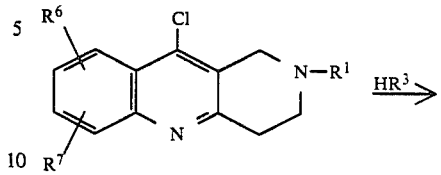

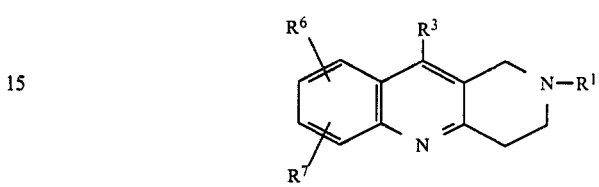

The starting materials used in the above outlined preparative sequences are all available commercially or can be prepared by conventional methods disclosed in the chemical literature.

The compounds used in the method of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, periodontal disease, tumor invasiveness, corneal ulcerations, epidermolysis bullosa and the like.

When the disclosed compounds are employed in the method of the invention as antiinflammatory agents, or collagenase inhibitors, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The interleukin 1 antagonist activity, as well as the antiinflammatory effects of the compounds used in the method of the invention may be demonstrated by standard pharmacological procedures, which are described more fully in the examples given hereinafter.

These procedures illustrate the ability of the compounds used in the invention to inhibit the IL 1-induced release of neutral protease from articular chondrocytes; and measure in vivo antiinflammatory activity of the compounds in the rat carageenan paw edema assay.

The following examples show the preparation and pharmacological testing of compounds used in the invention.

EXAMPLE 1

4-(7,10-Dichloro-3,4-dihydrobenzo[b][1,6]naphthyridin-2(1H)-yl)benzonitrile

A. 4-(1,4-Dioxa-8-azaspiro[4.5]dec-8-yl)benzonitrile

A mixture of 10 g (0.0825 mol) p-fluorobenzonitrile, 57 g (0.3282 mol) of 1,4-dioxa-8-azaspiro[4.5]decane, 17 g (0.123 mol) of $K_2CO_3$, and 100 ml of acetonitrile is stirred at 90°–100° C. for three days. The reaction mixture is allowed to cool to ambient temperature, diluted with water and extracted with methylene chloride. The combined extracts are washed with brine, dried over $Na_2SO_4$, and concentrated in vacuo to give a pasty solid. Trituration with ether furnishes 13.4 g (67%) of title compound: IR (KBr) 2210 and 1600 cm$^{-1}$; NMR (CDCl$_3$) $\delta$7.48 (d, 2H), 6.88 (d, 2H), 4.0 (s, 4H), 3.58–3.40 (m, 4H), and 1.90–1.70 (m, 4H).

B. 4-(4-Oxo-1-piperidinyl)benzonitrile

A mixture of 12 g (0.049 mol) of the ketal of step A, above, 120 ml of 10% sulfuric acid solution, and 60 ml of tetrahydrofuran is stirred at ambient temperature for 4 days. The reaction mixture is diluted with water and extracted with methylene chloride. The combined organic extracts are dried over $Na_2SO_4$ and concentrated in vacuo to give a pasty solid. Trituration with ether provides 4.6 g (46%) of title compound: IR (KBr) 2220 and 1700 cm$^{-1}$; NMR (CDCl$_3$) $\delta$7.54 (d, 2H), 6.90 (d, 2H), 3.88–3.66 (m, 4H), and 2.70–2.52 (m, 4H).

C. 4-(7,10-Dichloro-3,4-dihydrobenzo[b][1,6]naphthyridin-2(1H)-yl)benzonitrile To a slurry of 14.567 g (0.0849 mol) of 2-amino-4-chlorobenzoic acid and 71.22 ml of phosphorous oxychloride is added portionwise 17 g (0.0849 mol) of the compound of step B, above. The mixture is stirred under reflux for 3 hours and concentrated in vacuo. The residue is taken up in chloroform and poured carefully into a mixture of ice-NH$_4$OH and stirred for 30 minutes before extraction with chloroform. The combined extracts are washed with brine, dried over $Na_2SO_4$, and concentrated in vacuo to yield 26.48 g of solid. Purification by HPLC and trituration with ether furnishes 2.285 g (8%) of title compound as a yellow-orange solid: m.p. 209°–211° C.; IR (KBr) 3430, 2210, and 1604 cm$^{-1}$; NMR (CDCl$_3$) $\delta$8.19 (d, 1H), 8.08 (s, 1H), 7.61 (m, 3H), 7.03 (d, 2H), 4.75 (s, 2H), 3.87 (t, 2H), 3.57 (t, 2H).

Analysis for: $C_{19}H_{13}Cl_2N_3$ Calculated: C, 64.42; H, 3.70; N, 11.86. Found: C, 64.07; H, 3.69; N, 11.68.

EXAMPLE 2

4-(7,10-Dichloro-3,4-dihydrobenzo[b][1,6]naphthyridin-2(1H)-yl)benzoic acid ethyl ester

A. 4(1,4-Dioxa-8-azaspiro[4.5]dec-8-yl)benzoic acid ethyl ester

A mixture of 50 g (0.349 mol) of ethyl p-fluorobenzoate, 185 g (1.29 mol) of 1,4-dioxa-8-azaspiro[4.5]decane, 73 g (0.5282 mol) of $K_2CO_3$, and 400 ml of acetonitrile is stirred at 90°–100° C. for three days. The reaction mixture is allowed to cool to ambient temperature, diluted with water, and extracted with methylene chloride. The combined organic extracts are washed with brine, dried over $Na_2SO_4$, and concentrated in vacuo to give a pasty solid. Trituration with ether furnishes 31 g (23%) of title compound: IR (KBr) 1695 and 1610 cm$^{-1}$; NMR (CDCl$_3$) $\delta$7.98 (d, 2H), 6.96 (m, 2H), 4.36 (q, 2H), 4.02 (s, 4H), 3.58–3.48 (m, 4H), 1.92–1.80 (m, 4H), and 1.38 (t, 3H).

B. 4-(4-Oxo-1-piperidinyl)benzoic acid ethyl ester

A mixture of 2.7 g (0.0093 mol) of the ketal of step A, above, 30 ml of 10% sulfuric acid solution, and 15 ml of tetrahydrofuran is stirred at ambient temperature for 4 days. The reaction mixture is diluted with water and extracted with methylene chloride. The combined organic extracts are dried over $Na_2SO_4$ and concentrated in vacuo to give 1.2 g (52%) of title compound: IR (KBr) 1725 and 1695 cm$^{-1}$; NMR (CDCl$_3$) $\delta$8.04 (d, 2H), 7.96 (d, 2H), 4.38 (q, 2H), 3.98 (t, 4H), 2.6 (t, 4H), and 1.38 (t, 3H).

C. 4-(7,10-Dichloro-3,4-dihydrobenzo[b][1,6]naphthyridin-2(1H)-yl)benzoic acid ethyl ester To a slurry of 12.21 g (0.0712 mol) of 2-amino-4-chlorobenzoic acid and 60 ml of phosphorous oxychloride is added portionwise 17.6 (0.0712 mol) of the compound of step B, above. The mixture is stirred under reflux for 2½ hours and then concentrated in vacuo. The residue is taken up in chloroform and slowly added to an ice-NH$_4$OH mixture. The mixture is stirred for 30 minutes and then extracted with chloroform. The combined extracts are washed with brine, dried over $Na_2SO_4$, and concentrated in vacuo to yield 38.59 g of solid. Purification by HPLC furnishes 2.29 g (8%) of title compound as an orange solid: m.p. 155°–158° C. (dec.); IR (KBr) 1705, 1608, and 1282 cm$^{-1}$; NMR (CDCl$_3$) $\delta$8.20 (d, 1H), 8.05 (m, 3H), 7.59 (m, 1H), 7.04 (d, 2H), 4.76 (s, 2H), 4.37 (q, 2H), 3.88 (t, 2H), 3.37 (t, 2H), 1.38 (t, 3H).

Analysis for: $C_{21}H_{18}Cl_2N_2O_2$ Calculated: C, 62.85; H, 4.52; N, 6.98. Found: C, 62.52; H, 4.48; N, 6.98.

EXAMPLE 3

7,10-Dichloro-1,2,3,4-tetrahydro-2-(4-methylsulfonyl)-phenylbenzo[b][1,6]naphthyridine

A. 8-[4-(Methylsulfonyl)phenyl]-1,4-dioxa-8-azaspiro[4.5]-decane

A mixture of 10 g (0.057 mol) of p-fluorophenyl methyl sulfone, 8.72 g (0.063 mol) of $K_2CO_3$, 24.66 g (0.172 mol) of 1,4-dioxa-8-azaspiro[4.5]decane, and 50 ml of acetonitrile is stirred overnight at 90°–100° C. After cooling, the mixture is diluted with water and extracted with methylene chloride. The combined extracts are washed with brine, dried over $Na_2SO_4$, and concentrated in vacuo. Trituration with ether affords 13.11 g (77%) of title compound as a white solid: m.p. 192°–194° C.; IR (KBr) 1588, 1369, and 1290 cm$^{-1}$; NMR (CDCl$_3$) δ7.74 (m, 2H), 6.96 (m, 2H), 4.02 (s, 4H), 3.54 (m, 4H), 3.03 (s, 3H), 1.81 (m, 4H).

Analysis for: $C_{14}H_{19}NO_4S$ Calculated: C, 56.54; H, 6.44; N, 4.71. Found: C, 56.37; H, 6.55; N, 4.97.

B. 1-[4-(Methylsulfonyl)phenyl]-4-piperidinone

A mixture of 12.97 g (0.0436 mol) of the ketal of step A, above, and 200 ml of a 10% sulfuric acid/tetrahydrofuran (2:1) solution is stirred at 60°–70° C. for 4 hours and is then allowed to stand at room temperature for 3 days. The mixture is diluted with water and extracted with methylene chloride. The combined extracts are washed with brine, dried over $Na_2SO_4$, and concentrated in vacuo. Trituration with ether gives 10.07 g (91.1%) of title compound as a white solid: m.p. 183°–185° C.; IR (KBr) 3410, 1710, 1585, and 1160 cm$^{-1}$; NMR (CDCl$_3$) δ7.79 (d, 2H), 6.98 (d, 2H), 3.79 (t, 4H), 3.04 (s, 3H), 2.61 (t, 4H).

Analysis for: $C_{12}H_{15}NO_3S$ Calculated: C, 56.89; H, 5.97; N, 5.53. Found: C, 57.36; H, 6.23; N, 5.88.

C.
7,10-Dichloro-1,2,3,4-tetrahydro-2-(4-methylsulfonyl)-phenylbenzo[b][1,6]naphthyridine To a slurry of 6.46 g (0.0376 mol) of 2-amino-4-chlorobenzoic acid and 35 ml of phosphorous oxychloride is added portionwise 9.53 g (0.0376 mol) of the compound of step B, above. The mixture is stirred under reflux for 2 hours and concentrated in vacuo. The residue is dissolved in chloroform and slowly added to an ice-NH$_4$OH mixture. The mixture is stirred for 30 minutes before being extracted with chloroform. The combined extracts are washed with brine, dried over $Na_2SO_4$, and concentrated in vacuo to yield 9.92 g of solid. Purification by HPLC and trituration with ether furnishes 1.7 g (11%) of title compound as a light brown solid: m.p. 195°–198° C. (dec.); IR (KBr) 1592, 1296 and 1135 cm$^{-1}$; NMR (CDCl$_3$) δ8.18 (d, 1H), 8.07 (s, 1H), 7.86 (d, 2H), 7.59 (m, 1H), 7.09 (d, 2H), 4.78 (s, 2H), 3.89 (t, 2H), 3.37 (t, 2H), 3.02 (s, 3H).

Analysis for: $C_{19}H_{16}Cl_2N_2O_2S$ Calculated: C, 56.02; H, 3.96; N, 6.88. Found: C, 56.32; H, 3.97; N, 7.14.

EXAMPLE 4

7,10-Dichloro-2-(4-fluorophenyl)-1,2,3,4-tetrahydrobenz[b][1,6]naphthyridine

To a slurry of 13.32 g (0.0776 mol) of 2-amino-4-chlorobenzoic acid and 50 ml of phosphorous oxychloride is added slowly 15 g (0.0776 mol) of 1-(p-fluorophenyl)-4-piperidone. The mixture is stirred under reflux for 3 hours. The solution is concentrated in vacuo, dissolved in chloroform, and added to an ice-NH$_4$OH mixture. The mixture is stirred for ½ hour and extracted with chloroform. The combined extracts are washed with brine, dried over $Na_2SO_4$, and concentrated in vacuo to yield 34.36 g of solid. Purification by HPLC affords 3.97 g (15%) of title compound as a brown solid: m.p. 161°–164° C. (dec.); IR (KBr) 1604, 1510, and 1225 cm$^{-1}$; NMR (CDCl$_3$) δ8.16 (d, 1H), 8.06 (s, 1H), 7.55 (m, 1H), 7.05 (d, 4H), 4.54 (s, 2H), 3.66 (t, 2H), 3.34 (t, 2H).

Analysis for: $C_{18}H_{13}Cl_2FN_2$ Calculated: C, 62.26; H, 3.77; N, 8.07. Found: C, 62.07; H, 3.93; N, 8.02.

EXAMPLE 5

4-(10-Chloro-3,4-dihydrobenzo[b][1,6]naphthyridine-2(1H)-yl)benzonitrile, hemihydrate To a slurry of 3.424 g (25 mmol) of 2-aminobenzoic acid and 40 ml of phosphorous oxychloride is added portionwise 5 g (25 mmol) of the compound of Example 1, step B. The mixture is stirred under reflux for 3 hours and concentrated in vacuo. The residue is taken up in chloroform and poured carefully into a mixture of ice-NH$_4$OH and stirred for 30 minutes before extraction with chloroform. The combined extracts are washed with brine, dried over $Na_2SO_4$, and concentrated in vacuo to yield 5.36 g of solid. Purification by HPLC furnishes 0.17 g (2%) of title compound as a brown solid: m.p. 163°–165° C. (dec.); IR (KBr) 2210, 1650, and 1510 cm$^{-1}$; NMR (CDCl$_3$) δ8.25 (d, 1H), 8.08 (d, 1H), 7.78 (m, 1H), 7.69–7.52 (m, 3H), 7.03 (d, 2H), 4.77 (s, 2H), 3.87 (t, 2H), 3.37 (t, 2H).

Analysis for: $C_{19}H_{14}ClN_3 \cdot \frac{1}{2}H_2O$ Calculated: C, 69.41; H, 4.60; N, 12.78. Found: C, 69.31; H, 4.44; N, 12.48.

EXAMPLE 6

7,10-Dichloro-1,2,3,4-tetrahydro-2-[4-(trifluoromethyl)phenyl]benzo[b][1,6]naphthyridine, hemihydrate A. 1-[4-(trifluoromethyl)phenyl]-4-piperidinone A mixture of 25 g (0.1523 mol) of p-fluorobenzotrifluoride, 31 g (0.224 mol) of $K_2CO_3$, 65 g (0.4539 mol) of 1,4-dioxa-8-azaspiro[4.5]decane, and 150 ml of acetonitrile is stirred at reflux for 3 days. The reaction mixture is cooled, diluted with water, and extracted with methylene chloride. The combined extracts are washed with water, dried over $Na_2SO_4$ and concentrated in vacuo. The residue, 600 ml of 10% sulfuric acid solution and 300 ml of tetrahydrofuran is stirred at ambient temperature for 7 days, diluted with water and extracted with methylene chloride. The extracts are washed with brine, dried over $Na_2SO_4$, and concentrated in vacuo. Trituration with ether gives 0.9 g of title compound: IR (KBr) 1715, 1610, 1520 and 1330 cm$^{-1}$; NMR (CDCl$_3$) δ7.55 (d, 2H), 6.95 (d, 2H)m 3.73 (t, 4H), and 2.59 (t, 4H).

Analysis for: $C_{12}H_{12}NOF_3$ Calculated: C, 59.20; H, 4.97; N, 5.75. Found: C, 59.80; H, 5.45; N, 5.77.

B.
7,10-Dichloro-1,2,3,4-tetrahydro-2-[4-(trifluoromethyl)phenyl]benzo[b][1,6]naphthyridine, hemihydrate To a slurry of 350 mg (0.002 mol) of 2-amino-4-chlorobenzoic acid and 5 ml of phosphorous oxychloride is added portionwise 500 mg (0.0021 mol) of the compound of step A, above. The mixture is stirred under reflux for 4 hours and concentrated in vacuo. The residue is taken up in chloroform and poured carefully into a mixture of ice-NH$_4$OH and stirred for 30 minutes before extraction with chloroform. The combined extracts are washed with brine, dried over $Na_2SO_4$, and concentrated in vacuo to give 200 mg (27%) of title compound: IR (KBr) 1610, 1520, and 1330 cm$^{-1}$; NMR (DMSO-d$_6$) δ8.32 (d, 1H), 8.10 (m, 1H), 7.75 (d, 1H), 7.59 (d, 2H), 7.22 (d, 1H), 4.76 (s, 2H), 3.88 (t, 2H), and 3.24 (t, 2H).

Analysis for: $C_{19}H_{13}N_2Cl_2F_3 \cdot \frac{1}{2}H_2O$ Calculated: C, 56.17; H, 3.47; N, 6.90. Found: C, 56.04; H, 3.51; N, 7.20.

EXAMPLE 7

2-(7,10-Dichloro-3,4-dihydrobenzo[b][1,6]naphthyridin-2(1H)-yl)benzonitrile, hemihydrate

A. 2-(1,4-Dioxa-8-azaspiro[4.5]dec-8-yl)benzonitrile

A mixture of 23 g (0.0163 mol) o-fluorobenzonitrile, 70 g (0.4889 mol) of 1,4-dioxa-8-azaspiro[4.5]decane, 34 g (0.246 mol) of $K_2CO_3$, and 150 ml of acetonitrile is stirred at reflux for three days. The reaction mixture is allowed to cool to ambient temperature, diluted with water and extracted with methylene chloride. The combined extracts are washed with brine, dried over $Na_2SO_4$, and concentrated in vacuo to give an oil. Trituration with ether furnishes 15.6 g (39%) of title compound: IR (KBr) 2200, 1590 and 1485 cm$^{-1}$; NMR (CDCl$_3$) $\delta$7.65–6.9 (m, 4H), 4.02 (s, 4H), 3.33 (m, 4H), and 1.94 (m, 4H).

Analysis for: $C_{14}H_{16}N_2O_2$ Calculated: C, 68.83; H, 6.60; N, 11.47. Found: C, 68.64; H, 6.56; N, 11.49.

B. 2-(4-Oxo-1-piperidinyl)benzonitrile

A mixture of 15 g (0.0614 mol) of the ketal of A, above, 150 ml of 10% sulfuric acid solution, and 75 ml of tetrahydrofuran is stirred at ambient temperature for 7 days. The reaction mixture is diluted with water and extracted with methylene chloride. The combined organic extracts are dried over $Na_2SO_4$ and concentrated in vacuo to give a pasty solid. Trituration with ether provides 8.2 g (67%) of title compound: IR (KBr) 2200, 1705, 1590, and 1485 cm$^{-1}$; NMR (CDCl$_3$) $\delta$8.70–6.90 (m, 4H), 3.57 (t, 4H), and 2.72 (t, 4H).

Analysis for: $C_{12}H_{12}N_2O$ Calculated: C, 71.97; H, 6.04; N, 13.99. Found: C, 71.80; H, 6.12; N, 13.81.

C. 2-(7,10-Dichloro-3,4-dihydrobenzo[b][1,6]naphthyridin-2(1H)-yl)benzonitrile, hemihydrate To a slurry of 6.521 g (38 mmol) of 2-amino-4-chlorobenzoic acid and 40 ml of phosphorous oxychloride is added portionwise 7.61 g (38 mmol) of the compound of step B, above. The mixture is stirred under reflux for 3 hours and concentrated in vacuo. The residue is taken up in chloroform and poured carefully into a mixture of ice-NH$_4$OH and stirred for 30 minutes before extraction with chloroform. The combined extracts are washed with brine, dried over Na$_2$SO$_4$, and concentrated in vacuo to yield 14.2 g of solid. Purification by HPLC furnishes 0.34 g (3%) of title compound as a rust-colored solid: m.p. 132°–135° C.; IR (KBr) 2217, 1590, and 1448 cm$^{-1}$; NMR (CDCl$_3$) $\delta$8.17 (d, 1H), 8.07 (m, 1H), 7.69 (m, 1H), 7.59 (m, 2H), 7.21 (d, 1H), 7.12 (t, 1H), 7.64 (s, 2H), 3.81 (t, 2H), 3.46 (t, 2H).

Analysis for: $C_{19}H_{13}Cl_2N_3 \cdot \frac{1}{2}H_2O$ Calculated: C, 62.82; H, 3.88; N, 11.57. Found: C, 62.88; H, 4.06; N, 11.36.

EXAMPLE 8

4-(10-Chloro-3,4-dihydrobenzo[b][1,6]naphthyridin-2(1H)-yl)benzoic acid ethyl ester To a slurry of 0.296 g (5.8 mmol) of 2-aminobenzoic acid and 20 ml of phosphorous oxychloride is added slowly 1.435 g (5.8 mmol) of the compound of Example 2, step B. The mixture is stirred under reflux for 3 hours. The solution is concentrated in vacuo, dissolved in chloroform, and added to an ice-NH$_4$OH mixture. The mixture is stirred for $\frac{1}{2}$ hour and extracted with chloroform. The combined extracts are washed with brine, dried over Na$_2$SO$_4$, and concentrated in vacuo to yield 3.19 g of solid. Purification by HPLC affords 0.30 g (14%) of title compound as a solid: m.p. 130°–133° C.; IR (KBr) 1705 and 1610 cm$^{-1}$; NMR (CDCl$_3$) $\delta$8.27 (d, 1H), 8.07 (m, 3H), 7.79 (m, 1H), 7.66 (m, 1H), 7.05 (d, 2H), 4.79 (s, 2H), 4.37 (q, 2H), 3.89 (t, 2H), 3.40 (t, 2H), 1.39 (t, 3H).

Analysis for: $C_{21}H_{19}ClN_2O_2$ Calculated: C, 68.75; H, 5.22; N, 7.64. Found: C, 68.33; H, 5.20; N, 7.67.

EXAMPLE 9

4-(8,10-Dichloro-3,4-dihydrobenzo[b][1,6]naphthyridin-2(1H)-yl)benzonitrile, $\frac{1}{4}$ hydrate To a slurry of 6.427 g (37.5 mmol) of 2-amino-5-chlorobenzoic acid and 40 ml of phosphorous oxychloride is added portionwise 7.5 g (37.5 mmol) of the compound of Example 1, step B. The mixture is stirred under reflux for 3 hours and concentrated in vacuo. The residue is taken up in chloroform and poured carefully into a mixture of ice-NH$_4$OH and stirred for 30 minutes before extraction with chloroform. The combined extracts are washed with brine, dried over Na$_2$SO$_4$, and concentrated in vacuo to yield 8.79 g of solid. Purification by HPLC furnishes 1.32 g (9.9%) of title compound as a solid: m.p. 192°–197° C. (dec.); IR (KBr) 2230, 1615, and 1520 cm$^{-1}$; NMR (CDCl$_3$) $\delta$8.27 (m, 1H), 8.07 (m, 1H), 7.74 (m, 1H), 7.64 (d, 2H), 7.05 (d, 2H), 4.78 (s, 2H), 3.89 (t, 2H), 3.41 (t, 2H).

Analysis for: $C_{19}H_{13}Cl_2N_3 \cdot \frac{1}{4}H_2O$ Calculated: C, 63.61; H, 3.79; N, 11.71. Found: C, 63.56; H, 3.83; N, 11.48.

EXAMPLE 10

4-(10-Chloro-3,4-dihydro-7-methylbenzo[b][1,6]naphthyridin-2(1H)-yl)benzonitrile, 1/5 ethyl acetate To a slurry of 2.806 g (18.6 mmol) of 2-amino-4-methylbenzoic acid and 30 ml of phosphorous oxychloride is added portionwise 3.717 g (18.6 mmol) of the compound of Example 1, step B. The mixture is stirred under reflux for 3 hours and concentrated in vacuo. The residue is taken up in chloroform and poured carefully into a mixture of ice-NH$_4$OH and stirred for 30 minutes before extraction with chloroform. The combined extracts are washed with brine, dried over Na$_2$SO$_4$, and concentrated in vacuo to yield 4.32 g of solid. Purification by HPLC furnishes 0.78 g (12.6%) of title compound as a solid: m.p. 156°–159° C. (dec.); IR (KBr) 3400, 2190, and 1590 cm$^{-1}$; NMR (CDCl$_3$) $\delta$8.14 (d, 1H), 7.85 (s, 1H), 7.61 (d, 2H), 7.48 (m, 1H), 7.03 (m, 2H), 4.76 (s, 2H), 3.87 (t, 2H), 3.36 (t, 2H), 2.58 (s, 3H).

Analysis for: $C_{20}H_{16}ClN_3 \cdot 1/5 C_4H_8O_2$ Calculated: C, 71.08; H, 5.05; N, 11.96. Found: C, 71.51; H, 5.02; N, 11.63.

EXAMPLE 11

4-(10-Chloro-7-fluoro-3,4-dihydrobenzo[b][1,6]naphthyridin-2(1H)-yl)benzonitrile, $\frac{1}{4}$ hydrate To a slurry of 3.8 g (0.0215 mol) of 2-amino-4-fluorobenzoic acid and 22 ml of phosphorous oxychloride is added slowly 4.9 g (0.0245 mol) of the compound of Example 1, step B. The mixture is stirred under reflux for 3 hours. The solution is concentrated in vacuo, dissolved in chloroform, and added to an ice-NH$_4$OH mixture. The mixture is stirred for $\frac{1}{2}$ hour and extracted with chloroform. The combined extracts are washed with brine, dried over $Na_2SO_4$, and concentrated in vacuo. Purification by HPLC affords 505 mg (6%) of title compound as golden needles, m.p. 187°–188° C.; IR (KBr) 2200, 1600, 1510, 1490, and 1345 cm$^{-1}$; NMR (DMSO-d$_6$) δ8.30 (m, 1H), 7.9 (m, 1H), 7.7 (d, 2H), 7.65 (m, 1H), 7.21 (d, 2H), 4.8 (s, 2H), 3.92 (t, 2H), and 3.26 (t, 2H).

Analysis for: $C_{19}H_{13}ClFN_3 \cdot \frac{1}{4}H_2O$ Calculated: C, 66.67; H, 4.12; N, 12.28. Found: C, 66.92; H, 3.93; N, 12.14.

EXAMPLE 12

4-[7-Chloro-3,4-dihydro-10-(2-phenylhydrazino)benzo[b][1,6]naphthyridin-2(1H)-yl]benzonitrile, hydrate A solution of 5.7 g (0.016 mol) of the compound of Example 1, 16.5 ml (0.0167 mol) of phenylhydrazine, 4.7 ml of concentrated hydrochloric acid, and 150 ml of absolute ethanol is stirred at reflux temperature for 7 hours. On cooling, the resulting precipitate is collected, then dissolved in methanol. Treatment of this solution with $Na_2CO_3$ solution results in the formation of a precipitate. The solid is collected to afford 470 mg (7%) of title compound; m.p. 174°–177° C.; IR (KBr) 2205, 1600, 1560, and 1245 cm$^{-1}$; NMR (DMSO-d$_6$) δ8.70 (m, 2H, 1H exchangeable), 8.42 (s, 1H exchangeable), 7.84 (d, 1H), 7.60 (d, 2H), 7.42 (m, 1H), 7.28 (t, 2H), 7.04 (d, 2H), 6.90 (d, 2H), 6.84 (t, 1H), 4.68 (s, 2H), 3.78 (t, 2H), and 3.12 (t, 2H).

Analysis for: $C_{25}H_{20}ClN_5 \cdot H_2O$ Calculated: C, 67.63; H, 4.99; N, 15.78. Found: C, 67.64; H, 4.86; N, 15.55.

EXAMPLE 13

The ability of the compounds of the inventions to inhibit interleukin 1 is measured by the ability of the test compounds to inhibit the IL 1-induced release of neutral protease from rabbit articular chondrocytes.

This assay is carried out as follows:

Isolation of rabbit chondrocytes:

Male New Zealand White rabbits are anesthetized with 50 mg/kg of ketamine (i.m.) and killed by an intracardiac injection of 3 mls. of Nembutal. The knee joints of both legs are resected and the articular surfaces are exposed. Cartilage slices are obtained using a scalpel and are placed in a tissue culture dish (100 mm diameter) containing 10 mls of Hank's balanced salt solution (HBSS). The chondrocytes within the cartilage slices are then liberated by a series of enzyme digestions. The slices are incubated for 10 min. at 37° C. in 0.05% hyaluronidase (Sigma H-3884), rinsed with HBSS and incubated with 0.2% trypsin (Sigma T-2395) for 10 min. at 37° C. The slices are rinsed again and incubated for 10 mins. at 37° C. with 1.2% collagenase (Sigma C-5138). The slices are then rinsed again with HBSS and resuspended in 10 ml of Ham's F-12 medium containing 10% fetal bovine calf cerum (FCS) and 0.2% collagenase and incubated overnight at 37° C. in a 5% $CO_2$ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then plated into 24-well tissue culture plates ($2 \times 10^5$ cells/well) and incubated at 37° C. until confluent (usually 4–6 days).

Stimulation of chondrocytes and drug treatment:

The confluent chondrocytes are rinsed twice with serum-free Ham's F-12 medium and 1 ml is added to each well. Fifty μl of purified human IL 1 (100 Units/ml; Genzyme Corporation, Boston, MA) is then added to stimulate these cells to secrete neutral protease. To measure drug effects, the cells are treated with test compound 10 min. prior to addition of IL 1. The standard screening dose is 10 μM. Twenty-four hours after IL 1 stimulation, supernatant fluids are collected and assayed for neutral protease activity.

Neutral protease assay:

The neutral protease activity of chondrocyte supernatant fluids is determined by their ability to degrade an insoluble protease substrate, azocoll (Sigma). Supernatants are treated for 10 min. at room temperature with 350 μM p-aminophenylmurcuric acetate to activate the latent enzyme. Three hundred μl of supernatant is then mixed with 500 μl of a 20 mg/ml suspension of azocoll and incubated at 37° C. for 18–24 hrs. with gentle rocking. The mixtures are centrifuged and the amount of substrate hydrolyzed is determined by measuring the absorbance of the supernatant at 520 nm.

Drug effects are calculated as the % change in enzyme activity (absorbance) by supernatants from drug-treated chondrocytes relative to enzyme activity of supernatants from vehicle-treated chondrocytes as follows:

$$\% \text{ Inhibition of Protease Secretion} = \frac{(A_{520}) \text{ Untreated Supernatant} - A_{520} \text{ Drug treated Supernatant}}{A_{520} \text{ Untreated Supernatant}} \times 100$$

Where tested in this assay, the compounds of the invention gave the following results:

| Compound of Example No. | Dose (μM) | % Inhibition (I.S.D) |
|---|---|---|
| 1 | 10 | 22 ± 1 |
| 2 | 10 | 35 ± 16 |
| 3 | 10 | 62 ± 2 |
|   | 1 | 66 ± 1 |
|   | 0.1 | 69 ± 1 |
| 4 | 10 | 76 ± 29 |
|   | 1 | 9 ± 20 |
| 5 | 10 | 66 ± 29 |
| 8 | 10 | 91 |
|   | 1 | 43 |
|   | 0.1 | 40 |
| 9 | 10 | 86 |
|   | 1 | 43 |
| 10 | 10 | 33 |
| 11 | 10 | <20 |
| 12 | 10 | 69 |

The results show that the compounds tested exhibit a moderate to quite significant inhibition of IL 1-induced protease secretion.

What is claimed is:

1. A method for the treatment of inflammatory conditions and of collagenase-induced tissue destruction in warm-blooded animals which comprises the administration thereto of an anti-inflammatory/collagenase inhibitory amount of a compound having the formula

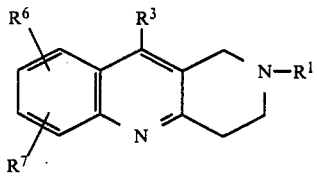

wherein

R[1] is phenyl or naphthyl, or phenyl or naphthyl substituted with halo, lower alkyl, lower alkyl carbonyl, benzoyl, carboxy, lower alkoxycarbonyl, $OR^2$, $N(R^2)_2$, $CON(R^2)_2$, $SO_3R^2$, $SO_2N(R^2)_2$, phenylsulfonyl, lower alkylsulfonyl, cyano, nitro or trifluoromethyl;

R[2] is hydrogen, lower alkyl or phenyl;

R[3] is halo, $R^4NNHR^5$, $NR^4R^5$, $OR^5$, $SR^5$, $R^4NCH_2CH_2OCH_3$ or $SCH_2CH_2CH_2NCH_2$;

R[4] is hydrogen or lower alkyl;

R[5] is hydrogen, lower alkyl, lower alkanoyl, lower cycloalkyl or phenyl; and

R[6] and R[7] are each independently, hydrogen, halo, nitro, lower alkoxy, lower alkyl, cyano, trifluoromethyl, phenyl, carboxy or lower alkoxycarbonyl.

2. The method of claim 1, wherein the compound administered is 4-(7,10-dichloro-3,4-dihydrobenzo[b][1,6]naphthyridin-2(1H)-yl)benzonitrile.

3. The method of claim 1, wherein the compound administered is 4-(7,10-dichloro-3,4-dihydrobenzo[b][1,6]naphthyridin-2(1H)-yl)benzoic acid ethyl ester.

4. The method of claim 1, wherein the compound administered is 7,10-dichloro-1,2,3,4-tetrahydro-2-(4-methylsulfonyl)phenylbenzo[b][1,6]naphthyridine.

5. The method of claim 1, wherein the compound administered is 7,10-dichloro-2-(4-fluorophenyl)-1,2,3,4-tetrahydrobenz[b][1,6]naphthyridine.

6. The method of claim 1, wherein the compound administered is 4-(10-chloro-3,4-dihydrobenz[b][1,6-]naphthyridine-2(1H)-yl)benzonitrile.

7. The method of claim 1, wherein the compound administered is 7,10-dichloro-1,2,3,4-tetrahydro-2-[4-(trifluoromethyl)phenyl]benzo[b][1,6]naphthyridine.

8. The method of claim 1, wherein the compound administered is 4-(10-chloro-3,4-dihydrobenzo[b][1,6-]naphthyridin-2(1H)-yl)benzoic acid ethyl ester.

9. The method of claim 1, wherein the compound administered is 4-(8,10-dichloro-3,4-dihydrobenzo[b][1,6]naphthyridin-2(1H)-yl)benzonitrile.

10. The method of claim 1, wherein the compound administered is 4-(10-chloro-3,4-dihydro-7-methylbenzo[b][1,6]naphthyridin-2(1H)-yl)benzonitrile.

11. The method of claim 1, wherein the compound administered is 4-(10-chloro-7-fluoro-3,4-dihydrobenzo[b][1,6]naphthyridin-2(1H)-benzonitrile.

12. The method of claim 1, wherein the compound administered is 4-[7-chloro-3,4-dihydro-10-(2-phenylhydrazino)benzo[b][1,6]naphthyridin-2(1H)-yl]benzonitrile.

* * * * *